United States Patent
Rouster et al.

(10) Patent No.: US 9,447,427 B2
(45) Date of Patent: Sep. 20, 2016

(54) PRODUCTION OF FATA TE-OVEREXPRESSING PLANTS WITH IMPROVED TOLERANCE TO WATER DEFICIT

(75) Inventors: Jacques Rouster, Mirefleurs (FR); Christophe Sallaud, Beaumont (FR); Sylvie Coursol, Paris (FR); Michel Zivy, Paris (FR); Laetitia Virlouvet, Epinay sur Orge (FR); Claude Welcker, Montferrier sur Lez (FR)

(73) Assignee: GENOPLANTE-VALOR, Paris (FR)

( * ) Notice: Subject to any disclaimer, the term of this patent is extended or adjusted under 35 U.S.C. 154(b) by 224 days.

(21) Appl. No.: 13/876,341

(22) PCT Filed: Oct. 14, 2011

(86) PCT No.: PCT/IB2011/054568
§ 371 (c)(1),
(2), (4) Date: Jun. 24, 2013

(87) PCT Pub. No.: WO2012/049661
PCT Pub. Date: Apr. 19, 2012

(65) Prior Publication Data
US 2013/0298283 A1    Nov. 7, 2013

(30) Foreign Application Priority Data
Oct. 15, 2010    (FR) ..................... 10 04058

(51) Int. Cl.
*C12N 15/82*    (2006.01)

(52) U.S. Cl.
CPC ....... *C12N 15/8273* (2013.01); *C12N 15/8247* (2013.01)

(58) Field of Classification Search
None
See application file for complete search history.

(56) References Cited

U.S. PATENT DOCUMENTS

2009/0094717 A1    4/2009    Troukhan et al.

FOREIGN PATENT DOCUMENTS

| WO | 01/38502 | | 5/2001 |
|---|---|---|---|
| WO | WO 01/38502 | * | 5/2001 |
| WO | 2007/049275 | | 5/2007 |

OTHER PUBLICATIONS

Tang, 2001, PhD thesis, University of Manitoba, pp. 1-176.*
Jing et al., 2011, BMC Biochemistry 12: 44, doi:10.1186/1471-2091-12-44.*
Dong et al., 2014, Gene 542: 16-22.*
Mayer and Shanklin, 2007, BMC Plant Biology 7:1, doi:10.1186/1471-2229-7-1.*
Arabidopsis thaliana clone AtFaTA, GenBank Accession No. NP 189147, published Aug. 21, 2009.*
Salas and Ohlrogge, 2002, Archives of Biochemistry and Biophysics 403: 25-34.*
Dörmann et al., 1995, Archives of Biochemistry and Biophysics 316: 612-618.*
Arabidopsis thaliana acyl-(acyl carrier protein) thioesterase clone TE 1-7, EMBL Accession No. Z36912, published Dec. 26, 1994.*
He et al., 2011, Cell Research 21: 442-465.*
Weinhold et al., 2013, BMC Plant Biology 13: 99.*

* cited by examiner

Primary Examiner — David T Fox
Assistant Examiner — Bratislav Stankovic
(74) Attorney, Agent, or Firm — Morgan, Lewis & Bockius LLP

(57) ABSTRACT

The present invention relates to a method for increasing the tolerance of a plant to water deficit, which method comprises the overexpression in said plant of a FatA TE (acyl-ACP thioesterase) protein.

10 Claims, 4 Drawing Sheets

```
                          1                                                50
B. distachyon         (1) MLRCHTPPQCRPAPLGRRG----LPRAAAEVVRCAARGSRRLPSLIVASS
T. aestivum           (1) MLRCHIPPQCGPAPLGRRGLPRAVR-CAARAPSRGAVAAAAAAAAQVAAA
O. sativa             (1) MLRCHTPPQCR---LGAGGAGAGVL-LRQRSEVAVRCRAQQVSGVEAAAG
S. bicolor FatA1      (1) MLRCPTQPQCGRAPLRHHGRRESPPSAAPGVVVRCARGAPQVSRIEAASP
S. bicolor FatA2      (1) MLRCHTPPQCGRAPLRHHGRRESPPAAAPGVVVRCARGAPQVPGIEAASP
Z. mays               (1) MLRCHAPPQCGRAPLRHHGRWESSP--APGVVVRCTRGAPQVSGIEAASP
Conserved a. a.       (1) MLRC    PQC    L   G                             A 51                                               100
B. distachyon        (47) SSAEAAVTCG---------ESLAERLRMGSLLEDGLSYKESFIVRCYEVGI
T. aestivum          (50) AVATAEG-----REGAERPGLAERLRMGSLLEDGLSYKESFIVRCYEVGI
O. sativa            (47) TPAARAA-----VEGGERTSLAERLRLGSLLEDGLSYKESFIVRCYEVGI
S. bicolor FatA1     (51) VAATTAAAAAKAERGDARPSLAERLRLGSLLEDGLSYKEIFIVRSYEVGI
S. bicolor FatA2     (51) GHAAATA--AKAEGGDARPSLAERLRLGSLLEDGLSYKESFIVRCYEVGI
Z. mays              (49) DHAAATAVAAKAEGGDARPSLAERLRLGSLLEDGLSYKESFIVRCYEVGI
Conserved a. a.      (51)    A             LAERLR G LLEDGLSYKE FIVR YEVGI 101                                              150
B. distachyon        (89) NKTATVETIANLLQEVGCNHAQSVGFSTDGFATTTTMRELGLIWVTNRMH
T. aestivum          (95) NKTATVETIANLLQEVGCNHAQSVGFSTDGFATTTTMRELGLIWVTNRMH
O. sativa            (92) NKTATVETIANLLQEVGCNHAQSVGFSTDGFATTTTMRKLGLIWVTNRMH
S. bicolor FatA1    (101) NKTATVETIANLLQEVGCSHAQSLGFSTDGFATTTSMRKLGLIWVTNRMH
S. bicolor FatA2     (99) NKTATVETIANLLQEVGCNHAQSVGFSTDGFATTTTMRKLGLIWVTNRMH
Z. mays              (99) NKTATVETIANLLQEVGCNHAQSVGFSTDGFATTTTMRKLGLIWVTNRMH
Conserved a. a.     (101) NKTATVETIANLLQEVGC HAQS GFSTDGFATTT MR LGLIWVTNRMH 151                                              200
B. distachyon       (139) IEIYKYPAWGDVVEIETWCQADGRIGTRRDWIIKDLASGEVIGRATSKWL
T. aestivum         (145) IEIYKYPAWGDVVEIETWCQADGKIGTRRDWILKDLANGEVIGRATSKWV
O. sativa           (142) IEIYKYPAWGDVVEIETWCQEDGKIGTRRDWILKDLANGEVIGRATSKWV
S. bicolor FatA1    (151) IEIYKYPAWGDVVEIETWCQADGRMGTRRDWILKDLANGEVIGRATSKWV
S. bicolor FatA2    (149) IEIYKYPAWGDVVEIETWCQEDGRIGTRRDWILKDLANGEVIGRATSKWV
Z. mays             (149) IEIYKYPAWGDVVEIETWCQEDGKIGTRRDWILKDLCTGEVTGRATSKWV
Conserved a. a.     (151) IEIYKYPAWGDVVEIETWCQ DG  GTRRDWI KDL  GEV GRATSKW 201                                              250
B. distachyon       (189) MMNQSTRRLQRVSDEVRDEVFVHCPKTPRLAFPEENNGSLKNIPILTDPA
T. aestivum         (195) MMNQNTRRLQRVSDEVRDEVFIHCPKSPRLAFPEENNGSLKKIPVLTDPA
O. sativa           (192) MMNQNTRRLQRVSDDVRDEVFVHCPKTPRLAFPEENNGSLKKIPVLTDPA
S. bicolor FatA1    (201) TMNQNTRRLQRVSDEVRDEVFIHCPKTPRLAFPEENNGSLKKIPNLSDSS
S. bicolor FatA2    (199) MMNQNTRRLQRVSDDVRDEVFIHCPKTPRLAFPEENNGSLKKIPNLSDPA
Z. mays             (199) MMNQNTRRLQRVSDDVRDEVFIHCPKTPRLAFPEENNGSLKKIPNLSDPA
Conserved a. a.     (201)  MNQ TRRLQRVSD VRDEVF HCPK PRLAFPEENNGSLK IP L D
```

Figure 1A

```
                         251                                                300
B. distachyon      (239) QYSRLGLVPRRADLDMNQHVNNVTYIGWVLESIPQDIIDTHELQTITLDY
T. aestivum        (245) QHSRLGLVPRRADLDMNQHVNNVTYIGWVLESIPQDIIDTHELQTITLDY
O. sativa          (242) QHSRLGLVPRRADLDMNQHVNNVTYIGWVLESIPQDIIDTHELQTITLDY
S. bicolor FatA1   (251) QYSRLGLVPRRADLDMNQHVNNVTYIGWVLESIPQDIIDTHELQTITLDY
S. bicolor FatA2   (249) QYSRLGLVPRRADLDMNQHVNNVTYIGWVLESIPQDIIDTHELQTITLDY
Z. mays            (249) QYSRLGLVPRRADLDMNQHVNNVTYIGWVLESIPQDIIDTHELQTITLDY
Conserved a. a.    (251) Q SRLGLVPRRADLDMNQHVNNVTYIGWVLESIPQDIIDTHELQTITLDY 301                                                350
B. distachyon      (289) RRECQHDDIVDSLTYVEEGEAKSSNGSAF-AAPHPQEQCQFLHCLRFAGG
T. aestivum        (295) RRECQHDDIVDSLTYIE-GEEINSNGSLF-SAPHPEEQRQFLHCLRFAGA
O. sativa          (292) RRECQHDDIVDSLTYIEEGEEKSSNGSAF-AAPHPEEQRQFLHCLRFAGN
S. bicolor FatA1   (301) RRECQYDDIVDSLTNVEEGEEKNMNGSAS-AAPHKEERQQFLHCLRFAAN
S. bicolor FatA2   (299) RRECQHDDIVDSLTYIEEGEEKSMNGSAS-AAPHKEERQQFLHCLRFAAN
Z. mays            (299) RRECQHDDIVDSLTYVEEGEERSMNGSAS-SVPHTEQRRQFLHCLRFAAN
Conserved a. a.    (301) RRECQ DDIVDSLT  E GE   NGS    PH    QFLHCLRFA 351         368         % identity     %similarity
B. distachyon      (338) GGELNRGRTVWR-KLSR-         78,9           85,2
T. aestivum        (343) GDEINRGRTVWR-KLAR-         81,4           84,7
O. sativa          (341) GNEINRGRTVWR-KLAR-         84,2           87
S. bicolor FatA1   (350) GAEINRGRTVWRRKLAR-         88,5           92,1
S. bicolor FatA2   (348) GDEINRGRTVWR-KLAR-         94,2           95,9
Z. mays            (348) GDEINRGRTVWR-KLAR-
Conserved a. a.    (351) G E NRGRTVWR KL R
```

Figure 1B

```
AtFatA1        ---MLKLSCNVTDSKLQRSLLFFSHSYRSDFVNFIRRRIVSCSQTKKTGLVPLRAVVSAD  57
AtFatA2        ---MLKLSCNVTDHIHN-----LFSNSRRIFVPVHRQTRPISCFQLKKE---PLRAILSAD  50
ZmFatA         MLRCHAPPQCGRAPLRHHGRWESSPAPGVVVRCTRGAPQVSGIEAASPDHAAATAVAAKA  60
Conserved a. a.                  *                    *                    *

AtFatA1        QGS-------VVQGLATLADQLRLGSLTEDGLSYKEKFVVRSYEVGSNKTATVETIANLLQ 111
AtFatA2        HGNSSVRVADTVSGTSPADRLRFGRLMEDGFSYKEKFIVRSYEVGINKTATIETIANLLQ 110
ZmFatA         EGG--------DARPSLAERLRLGSLLEDGLSYKESFIVRCYEVGINKTATVETIANLLQ 112
Conserved a. a.  *          *   ** *  *** **** * ** **** ***** ********

AtFatA1        EVGCNHAQSVGFSTDGFATTTMRKLHLIWVTARMHIEIYKYPAWGDVVEIETWCQSEGR 171
AtFatA2        EVACNHVQNVGFSTDGFATTLTMRKLHLIWVTARMHIEIYKYPAWSDVVEIETWCQSEGR 170
ZmFatA         EVGCNHAQSVGFSTDGFATTTMRKLGLIWVTNRMHIEIYKYPAWGDVVEIETWCQEDGK 172
Conserved a. a. ** *** * *********** ***** ***** ************ **********  *

AtFatA1        IGTRRDWILKDSVTGEVTGRATSKWVMMNQDTRRLQKVSDDVRDEYLVFCPQEPRLAFPE 231
AtFatA2        IGTRRDWILKDCATGEVIGRATSKWVMMNQDTRRLQRVTDEVRDEYLVFCPPEPRLAFPE 230
ZmFatA         IGTRRDWILKDLCTGEVTGRATSKWVMMNQNTRRLQRVSDDVRDEVFIHCPKTPRLAFPE 232
Conserved a. a. ***********  **** *********** ***** * * ****   ** *******

AtFatA1        ENNRSLKKIPKLEDPAQYSMIGLKPRRADLDMNQHVNNVTYIGWVLESIPQEIVDTHELQ 291
AtFatA2        ENNSSLKKIPKLEDPAQYSMLGLKPRRADLDMNQHVNNVTYIGWVLESIPQEIIDTHELK 290
ZmFatA         ENNGSLKKIPNLSDPAQYSRLGLVPRRADLDMNQHVNNVTYIGWVLESIPQDIIDTHELQ 292
Conserved a. a. *** ****** * ******  ** ************************** * *****

AtFatA1        VITLDYRRECQQDDVVDSLTTTTS-------EIGGTNGSATSGTQGHNDSQFLHLLRLSGD 345
AtFatA2        VITLDYRRECQQDDIVDSLTTSETPNEVVSKLTGTNGSTTSSKREHNESHFLHILRLSEN 350
ZmFatA         TITLDYRRECQHDDIVDSLTYVEE-----GEERSMNGSASSVPHTEQRRQFLHCLRFAAN 347
Conserved a. a. *********** ** *****          ***  *           *** **

% identity        % similarity
AtFatA1        GQEINRGTTLWRKKPSS 362         64,2              70,7
AtFatA2        GQEINRGRTQWRKKSSR 367         63,3              69,4
ZmFatA         GDEINRGRTVWRKLAR- 363
Conserved a. a. * ***** * ***
```

Figure 2

A
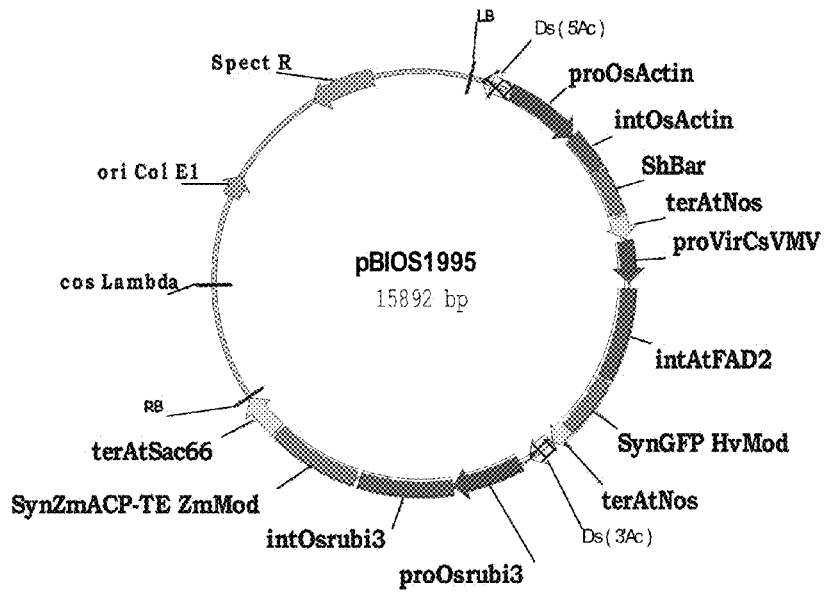
B
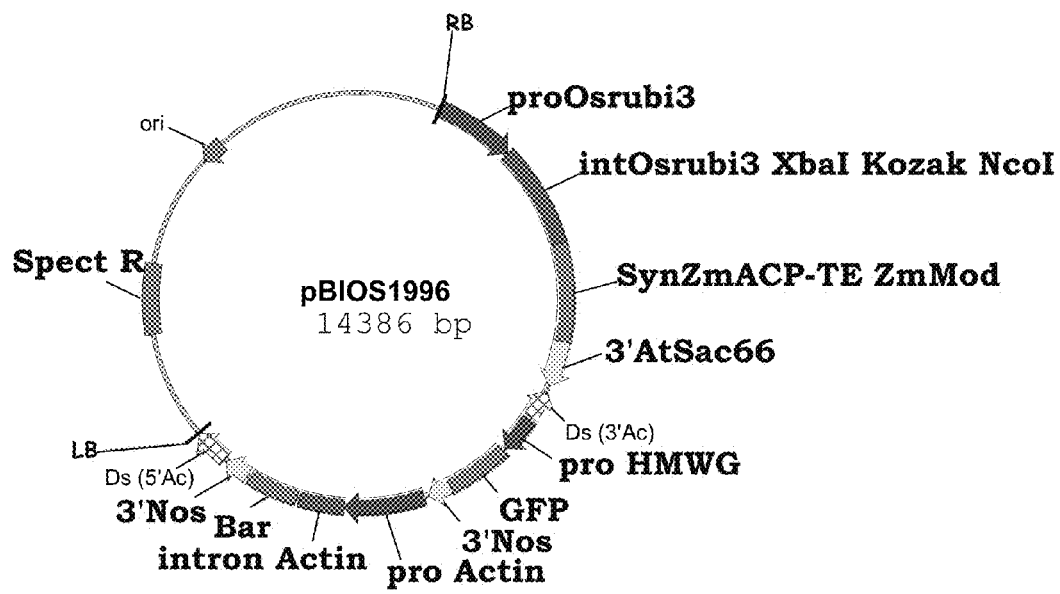
Figure 3

PRODUCTION OF FATA TE-OVEREXPRESSING PLANTS WITH IMPROVED TOLERANCE TO WATER DEFICIT

SEQUENCE LISTING SUBMISSION VIA EFS-WEB

A computer readable text file, entitled "045636-5226_SequenceListing.txt," created on or about 27 Mar. 2013, with a file size of about 27 kb contains the sequence listing for this application and is hereby incorporated by reference in its entirety.

The present invention relates to a method for producing plants tolerant to a water deficit.

"Water deficit" corresponds to a situation in which the amount of water transpired by a plant is greater than the amount of water absorbed by said plant.

Water deficit is one of the most important abiotic stresses for plants. It can affect the growth and the reproduction of the plants, thus resulting in a loss of yield.

Consequently, it is important to identify genes which have the ability to improve the tolerance of plants to water deficit.

ENR (enoyl-acyl carrier protein (ACP) reductase) and TE (acyl-ACP thioesterase, E.C. 3.1.2.14) proteins are involved in fatty acid biosynthesis in plants. ENR proteins convert 2,3-trans-enoyl-ACP into saturated acyl-ACP, and TE proteins hydrolyze the acyl half of ACP, releasing an ACP-SH and a fatty acid which will undergo other conversions via the pathway for long-chain fatty acid biosynthesis catalyzed by acyl-CoA synthetase. It has been shown that ENR and TE proteins interact physically together (Hellyer et al., Plant Mol. Biol., 20:763-780, 1992). They appear to constitute a metabolon which facilitates the transfer of substrates and products, and the simultaneous regulation (channeling) of enzymes involved in the fatty acid metabolic pathway (Brown et al., J. Exp. Bot., 57:1563-1571, 2006).

There are two major classes of TE proteins: the FatA class, the preferential substrate of which is oleic acid-ACP (18:1-ACP), and the FatB class, the preferential substrate of which is palmitic acid-ACP (16:0-ACP) (Beisson et al., Plant Physiol., 132:681-697, 2003).

In corn, a FatA TE protein (called ZmFatA), of which the gene encoding this protein is located on chromosome 2, has the peptide sequence represented by the sequence SEQ ID NO: 1.

Mayer and Shanklin (BMC Plant Biology, 7:1, 2007) have identified 4 amino acid residues in the peptide sequence of the TE proteins of *Arabidopsis thaliana* (amino acids in position 74, 86, 141 and 174) which, in plants, influence the substrate specificity between FatA TE proteins and FatB TE proteins. These 4 residues are respectively located at positions 108, 120, 175 and 208 in the amino acid sequence of ZmFatA (SEQ ID NO: 1).

During their studies, the inventors have demonstrated that transgenic corn (*Zea mays*) plants overexpressing the FatA TE protein (ZmFatA) exhibit increased tolerance to a water deficit compared with the wild-type (nontransgenic) corn plants.

The inventors have also demonstrated the orthologs of the ZmFatA protein in rice (*Oryza sativa*), sorgho (*Sorghum bicolor*), wheat (*Triticum aestivum*), Brachypodium distachyon and *Arabidopsis thaliana*.

The peptide sequence of the orthologs in monocotyledonous plants (e.g., sorgho, wheat and *Brachypodium*) has at least 78% identity or at least 84% similarity with the ZmFatA peptide sequence and comprises the conserved amino acids located at positions 1-4, 8-10, 15, 19, 46, 51, 69-74, 76-87, 89-92, 94-116, 118-121, 123-133, 135-136, 138-168, 170-171, 174-180, 182-184, 187-189, 191-197, 200-202, 204-212, 214-219, 221-224, 226-239, 241-242, 244, 246, 249, 251-303, 305-312, 315, 317-318, 323-325, 330-331, 337-345, 348, 350, 352-359, 360-361 and 363 of ZmFatA (SEQ ID NO: 1) when it is aligned with the ZmFatA protein (see FIGS. 1A and 1B).

The peptide sequence of the orthologs in *A. thaliana* (dicotyledonous plant) (Beisson et al., 2003, mentioned above) has at least 63% identity or at least 69% similarity with the ZmFatA peptide sequence and comprises the conserved amino acids located at positions 24, 55, 61, 70, 73-74, 76, 78, 80-82, 84-87, 89, 91-92, 94-97, 99-103, 105-114, 116-118, 120, 122-132, 134-138, 140-144, 146-157, 159-168, 171, 173-183, 186-189, 191-202, 204-208, 210, 212, 214-217, 222-223, 226-235, 237-242, 244, 246-251, 254-255, 257-283, 285, 287-291, 294-303, 305-306, 308-312, 323-325, 328, 338-340, 342-343, 348, 350-354, 356 and 358-360 of ZmFatA (SEQ ID NO: 1) when it is aligned with the ZmFatA protein (see FIG. 2).

Unless otherwise specified, the alignment between two peptide sequences and the calculation of the identity and similarity percentages are carried out over the entire length of the peptide sequences by means of the "needle" computer program (Needleman and Wunsch, J. Mol. Biol., 48, 443-453, 1970) using the default parameters: "Matrix": EBLOSUM62, "Gap penalty": 10.0 and "Extend penalty": 0.5.

The present invention consequently proposes to use the ZmFatA protein or an ortholog thereof to increase the resistance of plants to water deficit.

A subject of the present invention is a method for increasing the tolerance of a plant to water deficit, characterized in that a FatA TE protein, having at least 60% identity and, in increasing order of preference, at least 65%, 70%, 75%, 80%, 85%, 90%, 95%, 97%, 98% and 99% identity, or at least 70% similarity and, in increasing order of preference, at least 75%, 80%, 85%, 90%, 95%, 97%, 98% and 99% similarity with the sequence SEQ ID No. 1, is overexpressed in said plant.

According to one advantageous embodiment of the present invention, said FatA TE protein comprises the conserved amino acids located at positions 70, 73-74, 76, 78, 80-82, 84-87, 89, 91-92, 94-97, 99-103, 105-114, 116, 118, 120, 123-132, 135-136, 138, 140-144, 146-157, 159-168, 171, 174-180, 182-183, 187-189, 191-197, 200-202, 204-208, 210, 212, 214-217, 222-223, 226-235, 237-239, 241-242, 244, 246, 249, 251, 254-255, 257-283, 285, 287-291, 294-303, 305-306, 308-312, 323-325, 338-340, 342-343, 348, 350, 352-354, 356, 358-359 and 360 of said sequence SEQ ID No. 1 when it is aligned with said sequence SEQ ID No. 1.

According to another advantageous embodiment of the present invention, said FatA TE protein is derived from a monocotyledonous plant, and has at least 78% identity and, in increasing order of preference, at least 80%, 85%, 90%, 95%, 97%, 98% and 99% identity, or at least 84% similarity and, in increasing order of preference, at least 85%, 90%, 95%, 97%, 98% and 99% similarity with the sequence SEQ ID NO: 1 and comprises the conserved amino acids located at positions 1-4, 8-10, 15, 19, 46, 51, 69-74, 76-87, 89-92, 94-116, 118-121, 123-133, 135-136, 138-168, 170-171, 174-180, 182-184, 187-189, 191-197, 200-202, 204-212, 214-219, 221-224, 226-239, 241-242, 244, 246, 249, 251-303, 305-312, 315, 317-318, 323-325, 330-331, 337-345, 348, 350, 352-359, 360-361 and 363 of said sequence SEQ ID NO: 1 when it is aligned with said sequence SEQ ID NO: 1.

According to another advantageous embodiment of the present invention, said FatA TE protein is derived from a dicotyledonous plant, and comprises the conserved amino acids located at positions 24, 55, 61, 70, 73-74, 76, 78, 80-82, 84-87, 89, 91-92, 94-97, 99-103, 105-114, 116-118, 120, 122-132, 134-138, 140-144, 146-157, 159-168, 171, 173-183, 186-189, 191-202, 204-208, 210, 212, 214-217, 222-223, 226-235, 237-242, 244, 246-251, 254-255, 257-283, 285, 287-291, 294-303, 305-306, 308-312, 323-325, 328, 338-340, 342-343, 348, 350-354, 356 and 358-360 of said sequence SEQ ID NO: 1 when it is aligned with said sequence SEQ ID NO: 1.

The expression "a FatA TE protein derived from a monocotyledonous or dicotyledonous plant" is intended to mean a FatA TE protein expressed by a monocotyledonous or dicotyledonous plant or a synthetic FatA TE protein obtained by mutation of a FatA TE protein expressed by a monocotyledonous or dicotyledonous plant.

Said FatA TE protein is functional. The determination of a functional FatA TE protein can be carried out according to the method described by Mayer and Shanklin (BMC Plant Biology, 7:1, 2007). Briefly, a plasmid containing a gene encoding a FatA TE protein as defined above is introduced into the *E. coli* strain K27 (CGSC 5478). The transformed *E. coli* strains are then cultured in an appropriate medium. The content and the amount of the fatty acid methyl esters excreted into the culture medium by said strains is then determined.

According to another preferred embodiment of the present invention, said FatA TE protein is chosen from the group consisting of the following amino acid sequences:

SEQ ID NO: 1 (ZmFatA),
SEQ ID NO: 2 (FatA TE protein of *B. distachyon*),
SEQ ID NO: 3 (FatA TE protein of *T. aestivum*),
SEQ ID NO: 4 (FatA TE protein of *O. sativa*),
SEQ ID NOS: 5 and 6 (FatA TE proteins of *S. bicolor*),
SEQ ID NOS: 7 and 8 (FatA TE proteins of *A. thaliana*), and
SEQ ID NO: 8 (FatA TE protein of *A. thaliana*), more preferably SEQ ID NO: 1.

The present invention applies to all monocotyledonous or dicotyledonous plants, and in particular to plants sensitive to water deficit. In a nonlimiting manner, it can apply to edible plants, to ornamental plants, to fruit trees, to large crop plants such as wheat, corn or rice, or to industrial crop plants such as the cotton plant, rape or sunflower, preferably corn.

The overexpression (increase in expression) in a plant of a FatA TE protein as defined above can be carried out by modification of the genome of the said plant. This modification of the genome can in particular be carried out by genetic transformation of said plant with one or more copies of a polynucleotide encoding said protein, combined with cis regulatory sequences for its expression. The overexpression of said FatA TE protein can also be obtained by modification of the cis regulatory sequences for the expression of said FatA TE protein, for example by replacing its endogenous promoter with a stronger promoter, enabling a higher level of transcription, or else by attaching, to the endogenous promoter, transcription-activating sequences, of "enhancer" type, or translation-activating sequences.

In order to implement the method according to the present invention, use is made of an expression cassette comprising a polynucleotide encoding a FatA TE protein as defined above, placed under the transcriptional control of an appropriate promoter.

Said promoter can be a heterologous promoter. In this case, use may be made, for example, of:

constitutive promoters, such as the endosperm-specific high-molecular-weight glutenin promoter (Verdaguer et al., Plant Mol. Biol., 31:1129-1139, 1996), the CaMV 35S RNA promoter (Odell et al., Nature, 313: 810-812, 1985) or the CaMV 19S RNA promoter (Kay et al., Science, 236:1299-1302, 1987), the rice actin 1 promoter (McElroy et al., Plant Cell, 2:163-171, 1990), or the rice or corn ubiquitin 3 promoter (Sivamani and Qu, Plant Mol. Biol., 60:225-239, 2006), phloem-specific promoters, such as the Wheat Dwarf Virus promoter (Dinant et al., Physiologia plantarum 121:108-116, 2004; PCT application WO 03/060135) or the AtPP2-A1 promoter (Dinant et al., Plant Physiol., 131:114-128, 2003), leaf-specific promoters, such as the Rubisco small subunit promoter or the phosphoenolpyruvate carboxylase promoter, root-specific promoters, such as the rice RCc3 promoter (International application WO 2009/016104) or the rice antiquitin promoter (International application WO 2007/076115), or promoters locally inducible by stress (drought, salinity), such as the *Arabidopsis* rd29 promoter (Yamaguchi-Shinozaki and Shinozaki, Mol. Gen. Genet., 236: 331-340, 1993), preferably the endosperm-specific high-molecular-weight glutenin promoter.

It is also possible to use the promoter of another TE protein (for example, a FatB TE protein).

To implement the method according to the present invention, use may also be made of recombinant vectors resulting from the insertion of an expression cassette as described above into a host vector.

The expression cassettes and recombinant vectors as described above can, of course, also comprise other sequences, usually employed in constructs of this type. The choice of these other sequences will be made, conventionally by those skilled in the art according to, in particular, criteria such as the host cells selected, the transformation protocols envisioned, etc.

By way of nonlimiting examples, mention will be made of transcription terminators, leader sequences and polyadenylation sites. These sequences can be those which are naturally associated with the gene encoding the FatA TE protein as defined above, or else can be heterologous sequences. These sequences have no effect on the specific properties of the promoter or of the gene with which they are associated, but can qualitatively or quantitatively improve, overall, transcription and, where appropriate, translation. By way of examples of sequences of this type which are commonly used in plants, mention will be made, among the most widely used, of the CaMV 35S RNA terminator and the nopaline synthase gene terminator. It is also possible, for the purpose of increasing the expression level, to use transcription and translation enhancer sequences.

Among the other sequences commonly employed in the construction of expression cassettes and recombinant vectors mention will also be made of sequences for following the transformation, identification and/or selection of the transformed cells or organisms. These are in particular reporter genes, which confer a readily recognizable phenotype on the transformed cells or organisms, or else selectable marker genes: only the cells or organisms expressing a predetermined selectable marker gene are viable under given conditions (selective conditions). Reporter genes commonly employed are, for example, the beta-glucuronidase (GUS)

reporter gene, the luciferase reporter gene or the green fluorescent protein (GFP) reporter gene. Selectable marker genes are generally genes for resistance to an antibiotic, or also, in the case of plants or plant cells, to a herbicide. There is a very large variety of selectable marker genes from which those skilled in the art can choose according to the criteria that they will themselves have determined.

To implement the method according to the present invention, it is also possible to use host cells transformed with a polynucleotide encoding a FatA TE protein as defined above, which includes in particular host cells transformed with an expression cassette or a recombinant vector as described above.

The term "cell or organism transformed with a polynucleotide" is intended to mean any cell or organism of which the genetic content has been modified by transfer of said polynucleotide into said cell or said organism, whatever the method of transfer that was used, and whether the genetic information provided by said polynucleotide is integrated into the chromosomal DNA or remains extra chromosomal.

The host cells can be prokaryotic or eukaryotic cells. In the case of prokaryotic cells, they can in particular be agrobacteria, such as *Agrobacterium tumefaciens* or *Agrobacterium rhizobium*. In the case of eukaryotic cells, they can in particular be plant cells, derived from monocotyledonous or dicotyledonous plants.

The transgenic plants can be obtained by genetic transformation with at least one polynucleotide, one expression cassette or one recombinant vector as defined above. These transgenic plants comprise in their genome at least one copy of a transgene containing a polynucleotide as defined above.

A transgenic plant is defined here as a transformed plant in which the exogenous genetic information provided by a transforming polynucleotide is stably integrated into the chromosomal DNA, in the form of a transgene, and can thus be transmitted to the progeny of said plant. This definition therefore also encompasses the progeny of the plants resulting from the initial transgenesis, provided that they contain a copy of the transgene in their genome.

The plant material (protoplasts, calluses, cuttings, seeds, etc.) obtained from the transformed cells or from the transgenic plants are also part of the subject of the present invention. The invention also encompasses the products obtained from these transgenic plants, in particular the fodder, the wood, the leaves, the stems, the roots, the flowers and the fruits.

Various methods for producing transgenic plants are well known in themselves to those skilled in the art. Generally, these methods involve the transformation of plant cells, the regeneration of plants from the transformed cells, and the selection of the plants having integrated the transgene.

Many techniques for transforming germ-line or somatic plant cells (isolated, in the form of tissue or organ cultures, or on the whole plant) and regenerating the plants are available. The choice of the most appropriate method generally depends on the plant in question.

By way of nonlimiting examples of methods which are usable in the case of the plants mentioned above, it is possible to mention the protocols described by Guis et al. (Scientia Horticulturae 84: 91-99, 2000) for melon, by Hamza and Chupeau (J. Exp. Bot. 44: 1837-1845, 1993) for tomato, by Shoemaker et al. (Plant Cell Rep. 3: 178-181, 1986), by Trolinder and Goodin (Plant Cell Rep. 6: 231-234, 1987) for the cotton plant, by Van der Mark et al. (J. Genet Breeding 44: 263-268, 1990) or by Marchant et al. (Ann. Bot. 81: 109-114, 1998) for rose plants. In the case of monocotyledonous plants, mention may be made, for example of the protocols described by Hiei et al. (The Plant Journal, 6, 271-282, 1994) or Ishida et al. (Nature biotechnology, 14, 745-750, 1996) for corn, or by Rasco-Gaunt et al. (J. Exp. Bot. 52: 865-874, 2001) for wheat.

The present invention will be understood more clearly by means of the additional description which follows, which refers to nonlimiting examples illustrating the production of transgenic plants overexpressing the FatA TE protein as defined above and the demonstration of its role in increasing resistance to water deficit, and also the appended figures:

FIGS. 1A and 1B: alignment and percentage identity and similarity of the peptide sequences of the FatA TE proteins of *B. distachyon* (SEQ ID NO: 2), of *T. aestivum* (SEQ ID NO: 3), of *O. sativa* (SEQ ID NO: 4), of *S. bicolor* (SEQ ID NO: 5, FatA1 and SEQ ID NO: 6, FatA2) with the FatA TE protein of *Z. mays* (ZmFatA, SEQ ID NO: 1), using the "needle" computer program ("Matrix": EBLOSUM62, "Gap penalty": 10.0 and "Extend penalty": 0.5). The conserved amino acids (conserved a. a.) between all the peptide sequences are also represented.

FIG. 2: alignment and percentage identity and similarity of the peptide sequences of the FatA TE proteins of *A. thaliana* (SEQ ID NO: 7 [AtFatA1] and SEQ ID NO: 8 [AtFatA2]) with the FatA TE protein of *Z. mays* (ZmFatA, SEQ ID NO: 1), using the "needle" computer program ("Matrix": EBLOSUM62, "Gap penalty": 10.0 and "Extend penalty": 0.5). The conserved amino acids (conserved a. a.) between all the peptide sequences are represented by an asterisk (*).

FIG. 3: map of the binary vectors pBIOS1996 (A) and pBIOS1995 (B).

EXAMPLE 1

Production of Transgenic Corns Overexpressing the ZmFatA Protein

1) Cloning and Genetic Transformation of Corn

Two different transformation vectors (pBIOS 1562 and pBIOS 1958) were used for the genetic transformation of the corn. These vectors contain the *Streptomyces hygroscopicus* bar gene conferring resistance to the herbicide bialaphos (White et al., Nucleic Acids Res., 18:1062, 1990), which is of use for selecting the corn transformants, and a gene encoding a GFP (Green Fluorescent Protein) as a visual marker for following the presence of the transgene in the plants and the seeds. The difference between these two vectors lies in the cloning strategy used to introduce the expression cassette containing the gene of interest (cloning via the Gateway® system or restriction cloning) and the promoter for expression of the GFP (the cassava vein mosaic virus (CsVMV) promoter followed by the FAD2 intron of *Arabidopsis* or the endosperm-specific high-molecular-weight glutenin promoter).

According to a first cloning strategy, the synthetic gene encoding ZmFatA (SEQ ID No. 9; synthetic sequence optimized for expression in corn) containing the attL1 and attL2 restriction sites was introduced via an LR recombination reaction in the pBIOS 1562 Gateway binary destination vector, thus generating the pBIOS1995 vector (see FIG. 3A). The pBIOS 1562 vector is derived from the pSB12 vector (Komari et al., Plant J., 10:165-174, 1996) containing the bar gene under the control of the pActin promoter, the gene encoding a GFP under the control of the CsVMV promoter followed by the FAD2 intron, and the promoter and the 1$^{st}$ intron of rice ubiquitin 3 (Sivamani and Qu, Plant Mol. Biol., 60:225-239, 2006) followed by a Gateway cassette and by a polyadenylation sequence originating from the *Arabidopsis* Sac66 gene (Jenkins et al., Plant Cell Environ., 22:159-167, 1999).

According to a second cloning strategy, the synthetic gene encoding ZmFatA (SEQ ID No. 9) was introduced by restriction cloning (presence of SapI restriction sites between the coding region and the attL sites) into the pBIOS 1958 binary destination vector digested with SapI, thus generating the pBIOS1996 vector (see FIG. 3B). pBIOS 1958 is also derived from the pSB12 vector, but has the gene encoding a GFP under the control of the endosperm-specific high-molecular-weight glutenin promoter (HMWG promoter).

The pBIOS1995 or pBIOS1996 vector was then transferred into the *Agrobacterium tumefaciens* strain LBA4404 (pSB1) according to the method described by Komari et al., 1996 (mentioned above).

The corn cultivar A188 was then transformed with this strain of *agrobacterium* containing the pBIOS1995 vector or the pBIOS1996 vector, according to the method described by Ishida et al., 1996 (mentioned above). The primary transformants (T0) were selected according to routine methods as a function of the following four criteria:

(i) number of copies inserted: this determination was carried out by quantitative PCR. All the transformation events having more than 2 copies of the transgene were eliminated.

(ii) integrity of the T-DNA inserted: this was verified by means of a PCR reaction during the first steps of development of the transformed plant.

(iii) absence of premature termination of the transcription of the transgene: since each of the genes targeted is under the control of a constitutive promoter, it is possible to measure their expression using leaf tissues. The RNA of leaves from T0 plants was therefore extracted and the integrity of the transcripts was verified by RT-PCR using a sense primer located on the rice ubiquitin 3 intron and an antisense primer located on the AtSac66 terminator.

(iv) number of T1 grains harvested.

After selection of the transformants, 41 transgenic lines were obtained, 18 of which have a single and intact transgene.

2) Evaluation of the Tolerance of the Transgenic Plants to Water Deficit

First-generation plants (crossing of the primary transformant with the A188 recurrent line) are evaluated on a phenotyping platform. These transgenic plants are therefore hemizygous for the transgene (dominant trait of the genetic transformation). The controls ("RRS" and "RCP") used in the experiment correspond to the wild-type segregants resulting from this same cross.

2.1 Growing Compartment

The plants studied are cultivated in a phytotron. The latter, with a surface area of 30 m², has two independent growing chambers. In these chambers, the illumination, the temperature and the hygrometry are regulated (see section 2.2 below).

Sowing is carried out in earthenware containers with dimensions of 44×28.5×7 cm (H×W×L). Five genotypes are sown per earthenware container at a rate of ten seeds per genotype. Five plants only per genotype are used for the drying out kinetics.

2.2 Growing Conditions

Within the growing compartment, the temperature, the humidity and the illumination are regulated.

The conditions applied are the following:

Photoperiod:

Day for 16 h (6 am to 10 pm) with photosynthetic supplement (400 W sodium lamp) when the external radiation is less than 100 W/m².

Night for 8 h (10 μm to 6 am).

Thermoperiod: 24° C./20° C.

These conditions are adhered to by heating when the temperature is below 20° C. at night or 24° C. during the day, when the temperature exceeds 25° C.

Humidity: 75% relative humidity regulated by nocturnal fogging.

These various conditions ensure optimum growth of the corn.

2.3 Measurement of Drying Out Kinetics

Relevance of the Trait Measured:

The behavior of the plants with respect to transpiration is studied by means of continuous monitoring of the drop in relative water content (RWC) of small seedlings at a young stage (4 visible leaves). The objective is to study the response in terms of stomatal control of the plants when there is an abrupt interruption of water supply.

A very rapid stomatal control when a water deficit occurs makes it possible to save the available water, but limits the $CO_2$ assimilation capacity and therefore the production potential of the plant. On the other hand, quite late closing of the stomata makes it possible to maintain the photosynthetic activity of the plant ensuring the maintenance of the production potential, with the risk of said plant drying out more rapidly (Khalfaoui, 1991).

Method:

The measurements are carried out on whole T1 small seedlings at the 3-4 visible leaf stage. The plants used during this measurement are plants resulting from sowing in excess relative to the needs of the platform (3 seeds sown per pot). The numbers for the measurement of drying out are 5 plants per transformation event and wild-type controls.

The plants were cut at the neck, submerged for 24 hours at 4° C. in the dark (in order to saturate the cells with water) and then placed in a luminous climatic chamber regulated at 30° C.

The weight of the small seedlings is then monitored according to the timetable detailed in table II below:

TABLE II

Timetable of the weighing of small seedlings conditioned at 30° C. in full light. The weight at H0 corresponds to the weight at full turgidity. At the end of day 3, the small seedlings are placed in an incubator at 80° C. for 24 h in order to obtain, by means of a final weighing, the dry weight value.

| Day | Duration | | |
|---|---|---|---|
| 1 | H0 | ← | Weight full turgidity ($W_{Turg}$) |
| 1 | H0 + 2 | | |
| 1 | H0 + 6 | ← | Weight at time t ($W_t$) |
| 1 | H0 + 8 | | |
| 4 | H0 + 96 | ← | Dry weight ($W_d$) |

At time t, the relative water content of the plants is then calculated according to the following mathematical formula: $(W_t - W_d)/(W_{Turg} - W_d) \times 100$.

The invention claimed is:

1. A method for increasing the tolerance of a corn plant to water deficit, said method comprising overexpressing a FatA TE (acyl-ACP thioesterase) protein in said corn plant, wherein
said FatA TE protein is derived from a monocotyledonous plant, and has at least 95% amino acid sequence identity with the sequence of SEQ ID NO: 1, and comprises the conserved amino acids located at positions 1-4, 8-10, 15, 19, 46, 51, 69-74, 76-87, 89-92, 94-116, 118-121, 123-133, 135-136, 138-168, 170-171, 174-180, 182-184, 187-189, 191-197, 200-202, 204-212, 214-219, 221-224, 226-239, 241-242, 244, 246, 249, 251-303, 305-312, 315, 317-318, 323-325, 330-331, 337-345, 348, 350, 352-359, 360-361 and 363 of said sequence SEQ ID NO: 1 when aligned with said sequence SEQ ID NO: 1, or
said FatA TE protein is derived from a dicotyledonous plant, has at least 95% amino acid sequence identity with the sequence SEQ ID NO: 1 and comprises the conserved amino acids located at positions 24, 55, 61, 70, 73-74, 76, 78, 80-82, 84-87, 89, 91-92, 94-97, 99-103, 105-114, 116-118, 120, 122-132, 134-138, 140-144, 146-157, 159-168, 171, 173-183, 186-189, 191-202, 204-208, 210, 212, 214-217, 222-223, 226-235, 237-242, 244, 246-251, 254-255, 257-283, 285, 287-291, 294-303, 305-306, 308-312, 323-325, 328, 338-340, 342-343, 348, 350-354, 356 and 358-360 of said sequence SEQ ID NO: 1 when aligned with said sequence SEQ ID NO: 1, or said FatA TE protein comprises an amino acid sequence selected from the group consisting of the amino acid sequences SEQ ID NO: 2 to SEQ ID NO: 8 and
wherein said overexpression is obtained by
genetic transformation of said corn plant with one or more copies of a polynucleotide encoding said protein, combined with cis regulatory sequences for its expression.

2. The method as claimed in claim 1, wherein said FatA TE protein is derived from a monocotyledonous plant, and has at least 95% amino acid sequence identity with the sequence SEQ ID NO: 1, and comprises the conserved amino acids located at positions 1-4, 8-10, 15, 19, 46, 51, 69-74, 76-87, 89-92, 94-116, 118-121, 123-133, 135-136, 138-168, 170-171, 174-180, 182-184, 187-189, 191-197, 200-202, 204-212, 214-219, 221-224, 226-239, 241-242, 244, 246, 249, 251-303, 305-312, 315, 317-318, 323-325, 330-331, 337-345, 348, 350, 352-359, 360-361 and 363 of said sequence SEQ ID NO: 1 when aligned with the sequence of SEQ ID NO: 1.

3. The method as claimed in claim 1, wherein said FatA TE protein is derived from a dicotyledonous plant, has at least 95% amino acid sequence identity with the sequence SEQ ID NO: 1 and comprises the conserved amino acids located at positions 24, 55, 61, 70, 73-74, 76, 78, 80-82, 84-87, 89, 91-92, 94-97, 99-103, 105-114, 116-118, 120, 122-132, 134-138, 140-144, 146-157, 159-168, 171, 173-183, 186-189, 191-202, 204-208, 210, 212, 214-217, 222-223, 226-235, 237-242, 244, 246-251, 254-255, 257-283, 285, 287-291, 294-303, 305-306, 308-312, 323-325, 328, 338-340, 342-343, 348, 350-354, 356 and 358-360 of said sequence SEQ ID NO: 1 when aligned with said sequence SEQ ID NO: 1.

4. The method as claimed in claim 1, wherein FatA TE protein has at least 99% identity with the sequence of SEQ ID NO: 1.

5. The method as claimed in claim 1, wherein FatA TE protein comprises the sequence of SEQ ID NO: 1.

6. The method as claimed in claim 1, wherein the corn plant is transformed with an expression cassette comprising a polynucleotide encoding the FatA TE protein, placed under the transcriptional control of a promoter.

7. The method as claimed in claim 6, wherein the promoter is a heterologous promoter.

8. The method as claimed in claim 7, wherein the heterologous promoter is a constitutive promoter.

9. The method as claimed in claim 8, wherein the constitutive promoter is a rice ubiquitin 3 promoter.

10. The method as claimed in claim 1, wherein water deficit conditions are applied to said corn plant.

* * * * *

SEQUENCE LISTING

<160> NUMBER OF SEQ ID NOS: 9

<210> SEQ ID NO 1
<211> LENGTH: 363
<212> TYPE: PRT
<213> ORGANISM: Zea mays

<400> SEQUENCE: 1

```
Met Leu Arg Cys His Ala Pro Pro Gln Cys Gly Arg Ala Pro Leu Arg
1               5                   10                  15

His His Gly Arg Trp Glu Ser Ser Pro Ala Pro Gly Val Val Val Arg
            20                  25                  30

Cys Thr Arg Gly Ala Pro Gln Val Ser Gly Ile Glu Ala Ala Ser Pro
        35                  40                  45

Asp His Ala Ala Ala Thr Ala Val Ala Ala Lys Ala Glu Gly Gly Asp
    50                  55                  60

Ala Arg Pro Ser Leu Ala Glu Arg Leu Arg Leu Gly Ser Leu Leu Glu
65                  70                  75                  80

Asp Gly Leu Ser Tyr Lys Glu Ser Phe Ile Val Arg Cys Tyr Glu Val
                85                  90                  95

Gly Ile Asn Lys Thr Ala Thr Val Glu Thr Ile Ala Asn Leu Leu Gln
            100                 105                 110

Glu Val Gly Cys Asn His Ala Gln Ser Val Gly Phe Ser Thr Asp Gly
        115                 120                 125

Phe Ala Thr Thr Thr Thr Met Arg Lys Leu Gly Leu Ile Trp Val Thr
    130                 135                 140

Asn Arg Met His Ile Glu Ile Tyr Lys Tyr Pro Ala Trp Gly Asp Val
145                 150                 155                 160

Val Glu Ile Glu Thr Trp Cys Gln Glu Asp Gly Lys Ile Gly Thr Arg
                165                 170                 175

Arg Asp Trp Ile Leu Lys Asp Leu Cys Thr Gly Glu Val Thr Gly Arg
            180                 185                 190

Ala Thr Ser Lys Trp Val Met Met Asn Gln Asn Thr Arg Arg Leu Gln
        195                 200                 205

Arg Val Ser Asp Asp Val Arg Asp Glu Val Phe Ile His Cys Pro Lys
    210                 215                 220

Thr Pro Arg Leu Ala Phe Pro Glu Glu Asn Asn Gly Ser Leu Lys Lys
225                 230                 235                 240

Ile Pro Asn Leu Ser Asp Pro Ala Gln Tyr Ser Arg Leu Gly Leu Val
                245                 250                 255

Pro Arg Arg Ala Asp Leu Asp Met Asn Gln His Val Asn Asn Val Thr
            260                 265                 270

Tyr Ile Gly Trp Val Leu Glu Ser Ile Pro Gln Asp Ile Ile Asp Thr
        275                 280                 285

His Glu Leu Gln Thr Ile Thr Leu Asp Tyr Arg Arg Glu Cys Gln His
    290                 295                 300

Asp Asp Ile Val Asp Ser Leu Thr Tyr Val Glu Glu Gly Glu Arg
305                 310                 315                 320

Ser Met Asn Gly Ser Ala Ser Ser Val Pro His Thr Glu Gln Arg Arg
                325                 330                 335

Gln Phe Leu His Cys Leu Arg Phe Ala Ala Asn Gly Asp Glu Ile Asn
            340                 345                 350

Arg Gly Arg Thr Val Trp Arg Lys Leu Ala Arg
        355                 360
```

<210> SEQ ID NO 2
<211> LENGTH: 353
<212> TYPE: PRT
<213> ORGANISM: Brachypodium distachyon

<400> SEQUENCE: 2

Met Leu Arg Cys His Thr Pro Pro Gln Cys Arg Pro Ala Pro Leu Gly
1               5                   10                  15

Arg Arg Gly Leu Pro Arg Ala Ala Ala Glu Val Val Arg Cys Ala Ala
            20                  25                  30

Arg Gly Ser Arg Arg Leu Pro Ser Leu Ile Val Ala Ser Ser Ser Ser
        35                  40                  45

Ala Glu Ala Ala Val Thr Cys Gly Glu Ser Leu Ala Glu Arg Leu Arg
    50                  55                  60

Met Gly Ser Leu Leu Glu Asp Gly Leu Ser Tyr Lys Gly Ser Phe Ile
65                  70                  75                  80

Val Arg Cys Tyr Glu Val Gly Ile Asn Lys Thr Ala Thr Val Glu Thr
                85                  90                  95

Ile Ala Asn Leu Leu Gln Glu Val Gly Cys Asn His Ala Gln Ser Val
            100                 105                 110

Gly Phe Ser Thr Asp Gly Phe Ala Thr Thr Thr Met Arg Glu Leu
        115                 120                 125

Gly Leu Ile Trp Val Thr Asn Arg Met His Ile Glu Ile Tyr Lys Tyr
    130                 135                 140

Pro Ala Trp Gly Asp Val Val Glu Ile Glu Thr Trp Cys Gln Ala Asp
145                 150                 155                 160

Gly Arg Ile Gly Thr Arg Arg Asp Trp Ile Ile Lys Asp Leu Ala Ser
                165                 170                 175

Gly Glu Val Ile Gly Arg Ala Thr Ser Lys Trp Leu Met Met Asn Gln
            180                 185                 190

Ser Thr Arg Arg Leu Gln Arg Val Ser Asp Glu Val Arg Asp Glu Val
        195                 200                 205

Phe Val His Cys Pro Lys Thr Pro Arg Leu Ala Phe Pro Glu Glu Asn
    210                 215                 220

Asn Gly Ser Leu Lys Asn Ile Pro Ile Leu Thr Asp Pro Ala Gln Tyr
225                 230                 235                 240

Ser Arg Leu Gly Leu Val Pro Arg Ala Asp Leu Asp Met Asn Gln
                245                 250                 255

His Val Asn Asn Val Thr Tyr Ile Gly Trp Val Leu Glu Ser Ile Pro
            260                 265                 270

Gln Asp Ile Ile Asp Thr His Glu Leu Gln Thr Ile Thr Leu Asp Tyr
        275                 280                 285

Arg Arg Glu Cys Gln His Asp Asp Ile Val Asp Ser Leu Thr Tyr Val
    290                 295                 300

Glu Glu Gly Glu Ala Lys Ser Ser Asn Gly Ser Ala Phe Ala Ala Pro
305                 310                 315                 320

His Pro Gln Glu Gln Cys Gln Phe Leu His Cys Leu Arg Phe Ala Gly
                325                 330                 335

Gly Gly Gly Glu Leu Asn Arg Gly Arg Thr Val Trp Arg Lys Leu Ser
            340                 345                 350

Arg

<210> SEQ ID NO 3
<211> LENGTH: 358

<212> TYPE: PRT
<213> ORGANISM: Triticum aestivum

<400> SEQUENCE: 3

```
Met Leu Arg Cys His Ile Pro Pro Gln Cys Gly Pro Ala Pro Leu Gly
1               5                   10                  15

Arg Arg Gly Leu Pro Arg Ala Val Arg Cys Ala Ala Arg Ala Pro Ser
            20                  25                  30

Arg Gly Ala Val Ala Ala Ala Ala Ala Ala Gln Val Ala Ala
        35                  40                  45

Ala Ala Val Ala Thr Ala Glu Gly Arg Glu Gly Ala Glu Arg Pro Gly
    50                  55                  60

Leu Ala Glu Arg Leu Arg Met Gly Ser Leu Leu Glu Asp Gly Leu Ser
65                  70                  75                  80

Tyr Lys Glu Ser Phe Ile Val Arg Cys Tyr Glu Val Gly Ile Asn Lys
                85                  90                  95

Thr Ala Thr Val Glu Thr Ile Ala Asn Leu Leu Gln Glu Val Gly Cys
            100                 105                 110

Asn His Ala Gln Ser Val Gly Phe Ser Thr Asp Gly Phe Ala Thr Thr
        115                 120                 125

Thr Thr Met Arg Glu Leu Gly Leu Ile Trp Val Thr Asn Arg Met His
    130                 135                 140

Ile Glu Ile Tyr Lys Tyr Pro Ala Trp Gly Asp Val Val Glu Ile Glu
145                 150                 155                 160

Thr Trp Cys Gln Ala Asp Gly Lys Ile Gly Thr Arg Arg Asp Trp Ile
                165                 170                 175

Leu Lys Asp Leu Ala Asn Gly Glu Val Ile Gly Arg Ala Thr Ser Lys
            180                 185                 190

Trp Val Met Met Asn Gln Asn Thr Arg Arg Leu Gln Arg Val Ser Asp
        195                 200                 205

Glu Val Arg Asp Glu Val Phe Ile His Cys Pro Lys Ser Pro Arg Leu
    210                 215                 220

Ala Phe Pro Glu Glu Asn Asn Gly Ser Leu Lys Lys Ile Pro Val Leu
225                 230                 235                 240

Thr Asp Pro Ala Gln His Ser Arg Leu Gly Leu Val Pro Arg Arg Ala
                245                 250                 255

Asp Leu Asp Met Asn Gln His Val Asn Asn Val Thr Tyr Ile Gly Trp
            260                 265                 270

Val Leu Glu Ser Ile Pro Gln Asp Ile Ile Asp Thr His Glu Leu Gln
        275                 280                 285

Thr Ile Thr Leu Asp Tyr Arg Arg Glu Cys Gln His Asp Asp Ile Val
    290                 295                 300

Asp Ser Leu Thr Tyr Ile Glu Gly Glu Ile Asn Ser Asn Gly Ser
305                 310                 315                 320

Leu Phe Ser Ala Pro His Pro Glu Glu Gln Arg Gln Phe Leu His Cys
                325                 330                 335

Leu Arg Phe Ala Gly Ala Gly Asp Glu Ile Asn Arg Gly Arg Thr Val
            340                 345                 350

Trp Arg Lys Leu Ala Arg
        355
```

<210> SEQ ID NO 4
<211> LENGTH: 356
<212> TYPE: PRT
<213> ORGANISM: Oryza sativa

<400> SEQUENCE: 4

```
Met Leu Arg Cys His Thr Pro Pro Gln Cys Arg Leu Gly Ala Gly Gly
1               5                   10                  15

Ala Gly Ala Gly Val Leu Leu Arg Gln Arg Ser Glu Val Ala Val Arg
            20                  25                  30

Cys Arg Ala Gln Gln Val Ser Gly Val Glu Ala Ala Gly Thr Pro
        35                  40                  45

Ala Ala Arg Ala Ala Val Glu Gly Glu Arg Thr Ser Leu Ala Glu
    50                  55                  60

Arg Leu Arg Leu Gly Ser Leu Leu Glu Asp Gly Leu Ser Tyr Lys Glu
65                  70                  75                  80

Ser Phe Ile Val Arg Cys Tyr Glu Val Gly Ile Asn Lys Thr Ala Thr
                85                  90                  95

Val Glu Thr Ile Ala Asn Leu Leu Gln Glu Val Gly Cys Asn His Ala
                100                 105                 110

Gln Ser Val Gly Phe Ser Thr Asp Gly Phe Ala Thr Thr Thr Thr Met
            115                 120                 125

Arg Lys Leu Gly Leu Ile Trp Val Thr Asn Arg Met His Ile Glu Ile
130                 135                 140

Tyr Lys Tyr Pro Ala Trp Gly Asp Val Val Glu Ile Glu Thr Trp Cys
145                 150                 155                 160

Gln Glu Asp Gly Lys Ile Gly Thr Arg Arg Asp Trp Ile Leu Lys Asp
                165                 170                 175

Leu Ala Asn Gly Glu Val Ile Gly Arg Ala Thr Ser Lys Trp Val Met
            180                 185                 190

Met Asn Gln Asn Thr Arg Arg Leu Gln Arg Val Ser Asp Asp Val Arg
        195                 200                 205

Asp Glu Val Phe Val His Cys Pro Lys Thr Pro Arg Leu Ala Phe Pro
    210                 215                 220

Glu Glu Asn Asn Gly Ser Leu Lys Lys Ile Pro Val Leu Thr Asp Pro
225                 230                 235                 240

Ala Gln His Ser Arg Leu Gly Leu Val Pro Arg Arg Ala Asp Leu Asp
                245                 250                 255

Met Asn Gln His Val Asn Asn Val Thr Tyr Ile Gly Trp Val Leu Glu
            260                 265                 270

Ser Ile Pro Gln Asp Ile Ile Asp Thr His Glu Leu Gln Thr Ile Thr
        275                 280                 285

Leu Asp Tyr Arg Arg Glu Cys Gln His Asp Asp Ile Val Asp Ser Leu
    290                 295                 300

Thr Tyr Ile Glu Glu Gly Glu Glu Lys Ser Ser Asn Gly Ser Ala Phe
305                 310                 315                 320

Ala Ala Pro His Pro Glu Glu Gln Arg Gln Phe Leu His Cys Leu Arg
                325                 330                 335

Phe Ala Gly Asn Gly Asn Glu Ile Asn Arg Gly Arg Thr Val Trp Arg
            340                 345                 350

Lys Leu Ala Arg
        355

<210> SEQ ID NO 5
<211> LENGTH: 366
<212> TYPE: PRT
<213> ORGANISM: Sorghum bicolor

<400> SEQUENCE: 5
```

```
Met Leu Arg Cys Pro Thr Gln Pro Gln Cys Gly Arg Ala Pro Leu Arg
1               5                   10                  15

His His Gly Arg Arg Glu Ser Pro Pro Ser Ala Ala Pro Gly Val Val
            20                  25                  30

Val Arg Cys Ala Arg Gly Ala Pro Gln Val Ser Arg Ile Glu Ala Ala
        35                  40                  45

Ser Pro Val Ala Ala Thr Thr Ala Ala Ala Ala Lys Ala Glu Arg
50                  55                  60

Gly Asp Ala Arg Pro Ser Leu Ala Glu Arg Leu Arg Leu Gly Ser Leu
65                  70                  75                  80

Leu Glu Asp Gly Leu Ser Tyr Lys Glu Ile Phe Ile Val Arg Ser Tyr
                85                  90                  95

Glu Val Gly Ile Asn Lys Thr Ala Thr Val Glu Thr Ile Ala Asn Leu
            100                 105                 110

Leu Gln Glu Val Gly Cys Ser His Ala Gln Ser Leu Gly Phe Ser Thr
        115                 120                 125

Asp Gly Phe Ala Thr Thr Ser Met Arg Lys Leu Gly Leu Ile Trp
130                 135                 140

Val Thr Asn Arg Met His Ile Glu Ile Tyr Lys Tyr Pro Ala Trp Gly
145                 150                 155                 160

Asp Val Val Glu Ile Glu Thr Trp Cys Gln Ala Asp Gly Arg Met Gly
                165                 170                 175

Thr Arg Arg Asp Trp Ile Leu Lys Asp Leu Ala Asn Gly Glu Val Ile
            180                 185                 190

Gly Arg Ala Thr Ser Lys Trp Val Thr Met Asn Gln Asn Thr Arg Arg
        195                 200                 205

Leu Gln Arg Val Ser Asp Glu Val Arg Asp Glu Val Phe Ile His Cys
210                 215                 220

Pro Lys Thr Pro Arg Leu Ala Phe Pro Glu Glu Asn Asn Gly Ser Leu
225                 230                 235                 240

Lys Lys Ile Pro Asn Leu Ser Asp Ser Ser Gln Tyr Ser Arg Leu Gly
                245                 250                 255

Leu Val Pro Arg Arg Ala Asp Leu Asp Met Asn Gln His Val Asn Asn
            260                 265                 270

Val Thr Tyr Ile Gly Trp Val Leu Glu Ser Ile Pro Gln Asp Ile Ile
        275                 280                 285

Asp Thr His Glu Leu Gln Thr Ile Thr Leu Asp Tyr Arg Arg Glu Cys
290                 295                 300

Gln Tyr Asp Asp Ile Val Asp Ser Leu Thr Asn Val Glu Glu Gly Glu
305                 310                 315                 320

Glu Lys Asn Met Asn Gly Ser Ala Ser Ala Pro His Lys Glu Glu
                325                 330                 335

Arg Gln Gln Phe Leu His Cys Leu Arg Phe Ala Ala Asn Gly Ala Glu
            340                 345                 350

Ile Asn Arg Gly Arg Thr Val Trp Arg Arg Lys Leu Ala Arg
        355                 360                 365

<210> SEQ ID NO 6
<211> LENGTH: 363
<212> TYPE: PRT
<213> ORGANISM: Sorghum bicolor

<400> SEQUENCE: 6

Met Leu Arg Cys His Thr Pro Pro Gln Cys Gly Arg Ala Pro Leu Arg
```

```
               1               5              10              15
            His His Gly Arg Arg Glu Ser Pro Pro Ala Ala Pro Gly Val Val
                            20              25              30

Val Arg Cys Ala Arg Gly Ala Pro Gln Val Pro Gly Ile Glu Ala Ala
                            35              40              45

Ser Pro Gly His Ala Ala Thr Ala Ala Lys Ala Glu Gly Gly Asp
             50              55              60

Ala Arg Pro Ser Leu Ala Glu Arg Leu Arg Leu Gly Ser Leu Glu
             65              70              75              80

Asp Gly Leu Ser Tyr Lys Glu Ser Phe Ile Val Arg Cys Tyr Glu Val
                            85              90              95

Gly Ile Asn Lys Thr Ala Thr Val Glu Thr Ile Ala Asn Leu Leu Gln
                           100             105             110

Glu Val Gly Cys Asn His Ala Gln Ser Val Gly Phe Ser Thr Asp Gly
                           115             120             125

Phe Ala Thr Thr Thr Thr Met Arg Lys Leu Gly Leu Ile Trp Val Thr
             130             135             140

Asn Arg Met His Ile Glu Ile Tyr Lys Tyr Pro Ala Trp Gly Asp Val
            145             150             155             160

Val Glu Ile Glu Thr Trp Cys Gln Glu Asp Gly Arg Ile Gly Thr Arg
                           165             170             175

Arg Asp Trp Ile Leu Lys Asp Leu Ala Asn Gly Glu Val Ile Gly Arg
                           180             185             190

Ala Thr Ser Lys Trp Val Met Met Asn Gln Asn Thr Arg Arg Leu Gln
                           195             200             205

Arg Val Ser Asp Asp Val Arg Asp Glu Val Phe Ile His Cys Pro Lys
                           210             215             220

Thr Pro Arg Leu Ala Phe Pro Glu Glu Asn Asn Gly Ser Leu Lys Lys
            225             230             235             240

Ile Pro Asn Leu Ser Asp Pro Ala Gln Tyr Ser Arg Leu Gly Leu Val
                           245             250             255

Pro Arg Arg Ala Asp Leu Asp Met Asn Gln His Val Asn Asn Val Thr
                           260             265             270

Tyr Ile Gly Trp Val Leu Glu Ser Ile Pro Gln Asp Ile Ile Asp Thr
                           275             280             285

His Glu Leu Gln Thr Ile Thr Leu Asp Tyr Arg Arg Glu Cys Gln His
                           290             295             300

Asp Asp Ile Val Asp Ser Leu Thr Tyr Ile Glu Glu Gly Glu Lys
            305             310             315             320

Ser Met Asn Gly Ser Ala Ser Ala Ala Pro His Lys Glu Glu Arg Gln
                           325             330             335

Gln Phe Leu His Cys Leu Arg Phe Ala Ala Asn Gly Asp Glu Ile Asn
                           340             345             350

Arg Gly Arg Thr Val Trp Arg Lys Leu Ala Arg
                           355             360
```

<210> SEQ ID NO 7
<211> LENGTH: 362
<212> TYPE: PRT
<213> ORGANISM: Arabidopsis thaliana

<400> SEQUENCE: 7

```
            Met Leu Lys Leu Ser Cys Asn Val Thr Asp Ser Lys Leu Gln Arg Ser
            1               5              10              15
```

```
Leu Leu Phe Phe Ser His Ser Tyr Arg Ser Asp Pro Val Asn Phe Ile
            20                  25                  30

Arg Arg Arg Ile Val Ser Cys Ser Gln Thr Lys Lys Thr Gly Leu Val
        35                  40                  45

Pro Leu Arg Ala Val Val Ser Ala Asp Gln Gly Ser Val Val Gln Gly
    50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr Glu Val Gly
                85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
        115                 120                 125

Ala Thr Thr Thr Thr Met Arg Lys Leu His Leu Ile Trp Val Thr Ala
130                 135                 140

Arg Met His Ile Glu Ile Tyr Lys Tyr Pro Ala Trp Gly Asp Val Val
145                 150                 155                 160

Glu Ile Glu Thr Trp Cys Gln Ser Gly Arg Ile Gly Thr Arg Arg
                165                 170                 175

Asp Trp Ile Leu Lys Asp Ser Val Thr Gly Glu Val Thr Gly Arg Ala
            180                 185                 190

Thr Ser Lys Trp Val Met Met Asn Gln Asp Thr Arg Arg Leu Gln Lys
        195                 200                 205

Val Ser Asp Asp Val Arg Asp Glu Tyr Leu Val Phe Cys Pro Gln Glu
    210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Val Asp Thr His
        275                 280                 285

Glu Leu Gln Val Ile Thr Leu Asp Tyr Arg Arg Glu Cys Gln Gln Asp
290                 295                 300

Asp Val Val Asp Ser Leu Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
            340                 345                 350

Thr Thr Leu Trp Arg Lys Lys Pro Ser Ser
        355                 360

<210> SEQ ID NO 8
<211> LENGTH: 367
<212> TYPE: PRT
<213> ORGANISM: Arabidopsis thaliana

<400> SEQUENCE: 8

Met Leu Lys Leu Ser Cys Asn Val Thr Asp His Ile His Asn Leu Phe
1               5                   10                  15

Ser Asn Ser Arg Arg Ile Phe Val Pro Val His Arg Gln Thr Arg Pro
            20                  25                  30
```

```
Ile Ser Cys Phe Gln Leu Lys Lys Glu Pro Leu Arg Ala Ile Leu Ser
        35                  40                  45
Ala Asp His Gly Asn Ser Ser Val Arg Val Ala Asp Thr Val Ser Gly
 50                  55                  60
Thr Ser Pro Ala Asp Arg Leu Arg Phe Gly Arg Leu Met Glu Asp Gly
 65                  70                  75                  80
Phe Ser Tyr Lys Glu Lys Phe Ile Val Arg Ser Tyr Glu Val Gly Ile
                85                  90                  95
Asn Lys Thr Ala Thr Ile Glu Thr Ile Ala Asn Leu Leu Gln Glu Val
               100                 105                 110
Ala Cys Asn His Val Gln Asn Val Gly Phe Ser Thr Asp Gly Phe Ala
               115                 120                 125
Thr Thr Leu Thr Met Arg Lys Leu His Leu Ile Trp Val Thr Ala Arg
       130                 135                 140
Met His Ile Glu Ile Tyr Lys Tyr Pro Ala Trp Ser Asp Val Val Glu
145                 150                 155                 160
Ile Glu Thr Trp Cys Gln Ser Glu Gly Arg Ile Gly Thr Arg Arg Asp
               165                 170                 175
Trp Ile Leu Lys Asp Cys Ala Thr Gly Glu Val Ile Gly Arg Ala Thr
               180                 185                 190
Ser Lys Trp Val Met Met Asn Gln Asp Thr Arg Arg Leu Gln Arg Val
       195                 200                 205
Thr Asp Glu Val Arg Asp Glu Tyr Leu Val Phe Cys Pro Pro Glu Pro
       210                 215                 220
Arg Leu Ala Phe Pro Glu Glu Asn Asn Ser Ser Leu Lys Lys Ile Pro
225                 230                 235                 240
Lys Leu Glu Asp Pro Ala Gln Tyr Ser Met Leu Gly Leu Lys Pro Arg
               245                 250                 255
Arg Ala Asp Leu Asp Met Asn Gln His Val Asn Asn Val Thr Tyr Ile
               260                 265                 270
Gly Trp Val Leu Glu Ser Ile Pro Gln Glu Ile Ile Asp Thr His Glu
       275                 280                 285
Leu Lys Val Ile Thr Leu Asp Tyr Arg Arg Glu Cys Gln Gln Asp Asp
       290                 295                 300
Ile Val Asp Ser Leu Thr Thr Ser Glu Thr Pro Asn Glu Val Val Ser
305                 310                 315                 320
Lys Leu Thr Gly Thr Asn Gly Ser Thr Thr Ser Ser Lys Arg Glu His
               325                 330                 335
Asn Glu Ser His Phe Leu His Ile Leu Arg Leu Ser Glu Asn Gly Gln
               340                 345                 350
Glu Ile Asn Arg Gly Arg Thr Gln Trp Arg Lys Lys Ser Ser Arg
               355                 360                 365

<210> SEQ ID NO 9
<211> LENGTH: 1092
<212> TYPE: DNA
<213> ORGANISM: Artificial
<220> FEATURE:
<223> OTHER INFORMATION: synthetic sequence encoding ZmFatA

<400> SEQUENCE: 9
atgctgcgtt gccatgcacc accccagtgc ggtcgggctc ctctgcgcca tcacgggagg    60
tgggagagta gccagccccc tggtgttgtg gtgcgctgca ccagaggcgc accccaagtg   120
tccggcatag aggcggccag tccggaccat gccgctgcga ctgccgtcgc ggcaaaggct   180
```

```
gagggcggag atgcgaggcc ctcccttgct gagaggctca gattgggctc gcttctggag    240
gacgggctct cttacaagga gtcgttcata gtccgctgct acgaggtggg gatcaacaaa    300
accgcaacgg tggaaaccat cgccaatctg ctgcaagagg ttggatgcaa tcacgcacag    360
tccgtgggat tttctacgga cgggttcgct acgacgacga ccatgagaaa gcttggtctt    420
atttgggtga ctaaccgcat gcacattgag atttataagt atccggcgtg gggagatgtc    480
gtcgagatcg agacatggtg tcaagaagat ggcaagatcg ggaccaggcg cgattggatc    540
ctcaaggacc tctgtacagg cgaagtcacc ggcagggcta catctaagtg ggttatgatg    600
aatcaaaaca ctagaagatt gcagcgggtg agtgatgacg tccgcgatga agtgtttatc    660
cattgtccga aaacaccacg gctggcgttc ccggaagaga acaatggttc gctcaaaaag    720
atccctaact tgtcagatcc tgcccaatac tcaagactgg gcttggtgcc caggagggcc    780
gacctcgaca tgaaccagca tgtcaacaat gttacttaca ttggctgggt tttggagagc    840
attccgcagg acattataga tacccacgaa ctgcaaacga tcactcttga ttaccgtcgg    900
gaatgtcagc acgatgacat tgtcgactca ctgacctatg tggaggaagg ggaggaacgt    960
agcatgaacg gctcagcttc cagcgtccca cacactgagc agcgcaggca attcctccac   1020
tgtctgcgct tcgccgccaa cggtgatgaa atcaaccggg tcggacagt ttggcgcaag    1080 ctcgcgaggt ga                                                       1092
```